United States Patent [19]

De Simone et al.

[11] 4,029,709

[45] June 14, 1977

[54] PROCESS FOR THE HYDROGENATION OF CITRAL TO CITRONELLAL AND OF CITRONELLAL TO CITRONELLOL USING CHROMIUM-PROMOTED RANEY NICKEL CATALYST

[75] Inventors: Robert S. De Simone, Middletown, N.Y.; Peter S. Gradeff, Andover, N.J.

[73] Assignee: Rhodia, Inc., New York, N.Y.

[22] Filed: Feb. 17, 1976

[21] Appl. No.: 658,788

[52] U.S. Cl. .................... 260/601 R; 260/632 R; 260/631 H

[51] Int. Cl.² .................................. C07C 47/20

[58] Field of Search ....... 260/601 R, 632 R, 631 H, 260/631.5

[56] References Cited

UNITED STATES PATENTS

| | | | |
|---|---|---|---|
| 2,875,131 | 2/1959 | Carpenter | 260/599 |
| 3,275,696 | 9/1966 | Goldstein | 260/631.5 |
| 3,280,192 | 10/1966 | Levy | 260/599 |
| 3,346,650 | 10/1967 | Kane | 260/631.5 |
| 3,860,657 | 1/1975 | Easter et al. | 260/601 R |

*Primary Examiner*—James O. Thomas, Jr.
*Assistant Examiner*—W. B. Lone

[57] ABSTRACT

A process is provided for the semihydrogenation of the olefinic group in the conjugated position to the carbonyl group in citral and homologues thereof to form citronellal and homologues thereof, and also for the hydrogenation of the aldehyde group of citronellal to form citronellol and homologues thereof. The dienic aldehyde is hydrogenated with hydrogen in the presence of chromium-promoted Raney nickel catalyst, and optionally, an inert solvent such as a lower aliphatic alcohol. The process is of particular application to the hydrogenation of citral and citronellal to citronellol.

15 Claims, No Drawings

PROCESS FOR THE HYDROGENATION OF CITRAL TO CITRONELLAL AND OF CITRONELLAL TO CITRONELLOL USING CHROMIUM-PROMOTED RANEY NICKEL CATALYST that can be obtained from citral are shown in the following scheme:

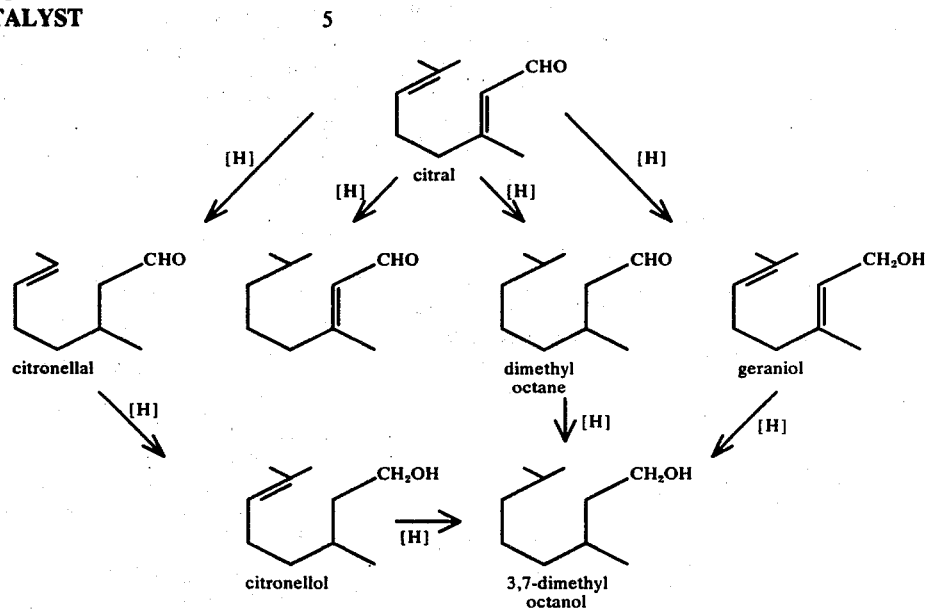

Citronellol is a valuable constituent of perfumes, and is extensively used. It occurs naturally in plants of the Rosaceae family. It has been reported to be present in about seventy essential oils. Reportedly, it constitutes more than 50% of Burgarian rose oil.

Synthetic citronellol can be produced from geraniol and/or nerol by hydrogenation with Raney cobalt catalyst, in accordance with the disclosure of U.S. Pat. No. 3,275,696, or with copper chromite at from 150° to 240° C in the presence of isopropanol, according to U.S. Pat. No. 3,346,650.

A paper published in Res. Ind. 1972 17(1), 11–12, reports the continuous hydrogenation of citral to citronellol using a fixed bed of copper chromium catalyst at pressures of from 25 to 50 kg/cm$^2$ and temperatures from 190° to 225° C, resulting in an approximately 70% yield of citronellol.

Citral is a particularly attractive starting material for citronellol, now that citral is available synthetically at relatively low cost.

Citral, 3,7-dimethyl-2-6-ocadiene-al, is a constituent of oil of lemon grass and it is also present to a limited extent in oils of verbena, lemon and orange. Until recently, the supply of citral has been dependent upon the availability of these oils. However, syntheses have now been developed which makes it possible to synthesize citral in high purity.

Citronellal is the semihydrogenation product of citral, obtained by hydrogenation of the 2-olefinic group in the conjugated position to the carbonyl group. However, the formation of citronellal by selective hydrogenation of the 2-olefinic group is difficult, because citral also has an ethylenic group in the 6-position, and a carbonyl group in conjugated position to the 2-ethylenic group, and all three of these groups are subject to hydrogenation. The various hydrogenation products In addition, citral and its hydrogenation derivatives can cyclize, yielding cyclic compounds such as isopulegol, in accordance with the following reaction:

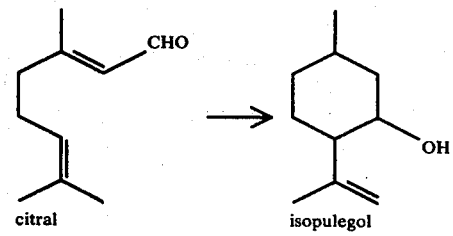

A retrol aldol condensation can also take place, in accordance with the following reaction:

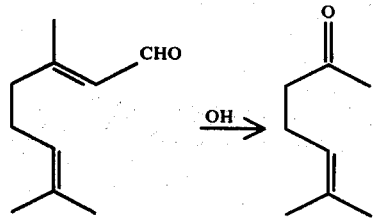

As a result of all of these various side reactions, the semihydrogenation of citral to citronellal, 3,7-dimethyl-6-octen-al, in good yield has proved difficult. In order to be suitable for commercial use, the process must be capable of economically producing sufficiently pure citronellal in good yield.

U.S. Pat. No. 3,971,830, patented July 27, 1976, to Gradeff, describes the preparation of citronella by semihydrogenation of citral in the presence of a palladium catalyst, a lower aliphatic alcohol, and aqueous alkali. In this process, the hydrogenation is quite selective. The amount of dimethyl octanal is only of the order of from 1 to 5%, and no citronellol is obtained.

It has been reported (J. Applied Chem. USSR 10, 119–25) that hydrogenation of citral can result in a 64% yield of citronellal, but such a yield is certainly unsatisfactory for use commercially. One of the problems is that the aldehyde group is sensitive and tends to be reduced to the alcohol. Moreover, the 6-ethylenic group can also be hydrogenated. This group is present in an aliphatic chain, and as such is available for attack.

In this respect, the semihydrogenation of citral differs from the hydrogenation of conjugated aromatic aldehydes such as cinnamic aldehydes in which the ethylenic double bond in the side chain is conjugated with the carbonyl group and also with the aromatic conjugation of the benzene ring. Levy and Friedman, U.S. Pat. No. 3,280,192, patented Oct. 18, 1966, discuss the problems that arise in this connection. They point out that the selective reduction of an olefinic linkage in the presence of a readily reducible group such as an aldehyde function usually cannot be achieved directly, and the catalytic hydrogenation of cinnamic aldehyde results in a variety of products and mixtures of products, of which the dihydrocinnamic aldehydes are only one component, including as well cinnamic alcohol, dihydrocinnamic alcohol and dihydrocinnamic aldehyde.

Levy and Friedman found that a highly selective hydrogenation of the double bond of cinnamic aldehyde and its lower alkyl substituted derivatives could be effected by employing palladium and an aqueous alkaline reaction medium for the hydrogenation. When such a combination is used, the hydrogenation proceeds with substantially no formation of the undesirable alcohol by-product, and the process finds an automatic end point in that the absorption of hydrogen ceases when only the olefinic double bond is saturated.

Levy and Friedman in British Pat. No. 1,086,447, published Oct. 11, 1967, extend the disclosure of No. 3,280,192 somewhat, and indicate that citronellal (dimethyl octanol) can be hydrogenated to citronellol in their process, at 50° to 80° C., using aqueous sodium carbonate solution and palladium on charcoal, in a 93.5% yield. This suggests that the aldehyde group of citronellal is hydrogenated under their reaction conditions, even in the absence of the alcohol solvent (in the presence of which they had indicated in No. 3,280,192, cinnamic aldehyde is converted to an alcohol), and also the olefinic group is hydrogenated.

Easter et al U.S. Pat. No. 3,860,657, patented Jan. 14, 1975, describe the hydrogenation of citral in good yield, with very little unconverted citral, very little dimethyl octanal, and practically no citronellol, isopulegol or dimethyl octanol, by using a palladium catalyst in the presence of a small amount of water and a base. Strong, moderately strong, and weak bases can be used, as well as organic amines. In the Examples, however, no yield data are given, merely the analysis of the composition of the product by vapor phase chromatography, which gives no indication of the amount of polymer or other nonvolatile residue formed.

The use of Raney nickel-type catalyst is disclosed in the Easter et al patent No. 3,860,657, Example XI. The Example was included for purposes of comparison with the palladium catalyst in the process of the Easter et al invention, and shows that the Raney nickel-type catalyst has quite poor selectivity for the hydrogenation of citral. In the Example, pure citral (152 grams), (from the same source as utilized in Example) and 5 grams of Raney nickel-type catalyst were hydrogenated at 70° C and 50 psi hydrogen pressure. In 6½ hours, about the stoichiometric amount of hydrogen for hydrogenation of citral to citronellal had been added. The reaction product, by VPC, showed the following analysis:
 DMA 2 percent
 Citronellal 55 percent
 Citral 18 percent
 Citronellol 25 percent Apparently, the hydrogenation in the presence of Raney nickel is slow (18% citral remaining after 6½ hours) and accompanied by a substantial amount of DMA.

It is apparent that the usual Raney nickel-type catalyst is not as satisfactory as palladium, and gives poor yields, in addition to poor selectivity.

In accordance with the instant invention, a process is provided for the selective hydrogenation of the olefinic group in the conjugated position to the carbonyl group in citral and homologous dienic aldehydes, and for the hydrogenation of the aldehyde group in citronellal and homologous ethylenic aldehydes, accomplished in the presence of chromium-promoted Raney nickel catalyst and hydrogen gas, suitably but not necessarily in an inert organic solvent as the reaction medium. The reaction proceeds at room temperature and at atmospheric pressure, although lower or higher temperatures and higher pressures can be used, if desired.

If the hydrogenation is stopped early enough, for instance, immediately after all of the citral is gone, citronellol is found in admixture with citronellal and can be recovered in high purity and substantially without contamination by dimethyl octanol. Thus the process provides also a method for preparation of citronellal in admixture with citronellol essentially free of other by-products such as DMO.

Both citronellal and citronellol can be prepared separately or in admixture by the process of the invention, starting from citral, and can be obtained in high purity and substantially without contamination by dimethyl octanol.

The process of the invention is applicable to citral and to homologous dienic aldehydes and to citronellal and to homologous ethylenic aldehydes having the formulae:

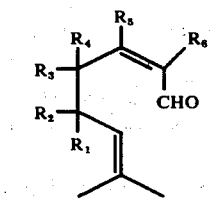 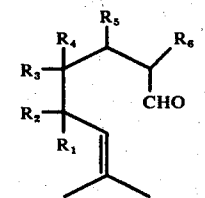

wherein $R_1$, $R_2$, $R_3$, $R_4$, and $R_6$ are selected from the group consisting of hydrogen and lower alkyl groups having from one to about five carbon atoms and $R_5$ is a lower alkyl group having from one to about five carbon atoms. The R alkyl groups can be straight chain or branched chain.

Exemplary R alkyl groups include methyl, ethyl, propyl, isopropyl, butyl, sec-butyl, isobutyl, amyl, isoamyl, and tert-amyl.

The process of the invention is of particular application to citral, 3,7-dimethyl-2,6-octadiene-al which can be converted to citronelal and citronellol, or completely to citronellol, in yields in excess of 95%. In the case of citral and citronellal, the reaction proceeds as follows:

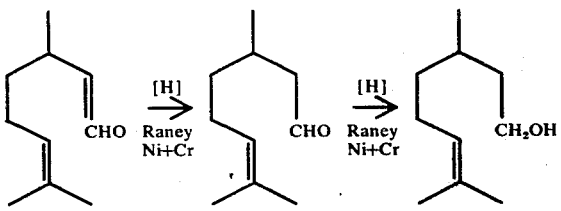

The process is applicable to both geometric isomers of citral, geranial and neral, as well as to the lower alkyl homologues of citral.

Other dienic aldehydes to which the invention is applicable include:
3-ethyl-7-methyl-2,6 octadiene-al
3-isobutyl-7-methyl-2,6-octadiene-al
3-amyl-7-methyl-2,6-octadiene-al
2,3,4,5,7-pentamethyl-2,6-octadiene-al
3,5,7-trimethyl-2,6-octadiene-al
3,4,4,5,5,7-hexamethyl-2,6-octadiene-al
2,4,7-trimethyl-3-isopropyl-2,6-octadiene-al
2,3,7-trimethyl-2,6-octadiene-al Other ethylenic aldehydes to which the invention is applicable include:
3-ethyl-7-methyl-6-octene-al
3-isobutyl-7-methyl-6-octene-al
3-amyl-7-methyl-6-octene-al
2,3,4,5,7-pentamethyl-6-octene-al
3,5,7-trimethyl-6-octene-al
3,4,4,5,5,7-hexamethyl-6-octene-al
2,4,7-trimethyl-3-isopropyl-6-octene-al
2,3,7-trimethyl-6-octene-al The chromium is essential. Raney nickel that contains only nickel and aluminum is nonselective, as noted by Easter et al in U.S. Pat. No. 3,860,657. See the Examples below.

The chromium-promoted Raney nickel catalyst is known, and is available commercially. The catalyst is an alloy of nickel, aluminum and chromium; some iron may be present also; iron is ineffectual but nondeleterious. The aluminum of the alloy is digested with aqueous sodium hydroxide via the known procedure, and the remaining Ni-Cr used for the hydrogenation. The catalyst is also sold in its active form, the alkali digestion of the alloy of nickel aluminum and chromium having already been done, the Ni-Cr washed, and preserved in aqueous suspension.

The active chromium-promoted Raney nickel catalyst can be used without a support, but if desired, a suitable inert support can be used. Such supports are also conventional, and include, for example, carbon, silica gel, barium, charcoal, calcium carbonate, aluminum sulfate, and kieselguhr.

A small amount of the catalyst is quite sufficient. The larger the amount of catalyst used, the more rapid the rate of hydrogenation. Also, the more active the catalyst used, the greater the effect on the rate of hydrogenation. It is well known that freshly-prepared Raney nickel catalysts are more active than catalysts that have been stored for some time.

Satisfactory results are obtained with amounts of catalyst as small as 1% by weight of the citral or citronellal or homologue thereof; in some cases, amounts as small as 0.5% by weight can be used.

Normally, an amount in excess of about 25% by weight of the citral or citronellal or homologues thereof is not required, and in most cases, an amount within the range from about 2 to about 15% by weight is preferred.

The reaction can be carried out at from about 5° C to about room temperature, but is faster at elevated temperatures. There is no upper limit on reaction temperature, except that imposed by the stability of the starting aldehyde and/or the reaction product. Temperatures from about 20° up to about 100° C are preferred, but the reaction temperature may in some cases be as high as 200° C.

The reaction proceeds rather rapidly, depending upon temperature, hydrogen concentration, and catalyst concentration. Usually, the reaction does not require more than twenty hours for completion, and depending upon the end product desired, may be complete in as little as one-half hour.

In order to avoid poisoning the catalyst, and reducing its activity, it is desirable that the citral or citronellal starting material be neutral. Any acidity can be removed by washing the citral or citronellal or homologue thereof with water or aqueous alkali.

The hydrogenation can be carried out in the absence of a solvent. However, better selectivity and a higher yield of citronellal and/or citronellol is obtained if an inert solvent is used. The lower alkanols having from one to about four carbon atoms are preferred, such as methanol, ethanol, propanol, butanol, and isobutanol. However, any inert organic solvent in which the starting material and/or the reaction products are soluble can be used. Aliphatic hydrocarbons such as hexane, pentane and octane, and cyclic ethers such as tetrahydrofuran and dioxane, can be used with good results.

Usually, an amount of solvent at least about 10% by weight of the starting aldehyde increases yield satisfactorily. There is no upper limit on the amount, and the solvent can be present in a considerable excess. However, unduly dilute solutions increase handling difficulties, because of the greater volumes of material, and are not normally practical. Consequently, the amount of solvent is usually not in excess of about 200%, and preferably is not in excess of about 100%, by weight of the dienic or ethylenic aldehyde starting material.

The reaction can be begun by charging the citral or citronellal or homologue, any inert solvent (such as the lower alkanol), and the chromium-promoted Raney nickel catalyst, into a suitable pressure vessel equipped with stirring and optionally with heating facilities. A hydrogen atmosphere is then provided, and hydrogen supplied to the system under pressure for a time sufficient to produce the desired reaction product. If the starting material is citral, citronellal is formed in largest amounts in the initial stages of the reaction, and then the amount of citronellol starts to build up, so that if citronellol is a desired product, a longer reaction time is required than if citronellal is the only desired product. Over a considerable range of reaction times, both citronellal and citronellol can be obtained together as reaction products, in admixture. Citronellol is obtained either from citronellal or from citral in yields higher than 90%, accompanied usually by some 2 to 4% geraniol and nerol. There are also perfume components, and are usually found in a perfume-grade citronellol, so that extensive purification is not required.

The hydrogenation of citral can be carried out to form mixtures of citronellal and citronellol, or citronellol exclusively. As the amount of citronellol increases, small amounts of dimethyl octanol tend to be formed, and consequently, if this impurity is not desired, it is well to halt the hydrogenation at a stage before dimethyl octanol begins to be formed, but preferably after all the citral has been converted.

The hydrogenation can be stopped early and preferably after all of the citral has disappeared. The fractionation of mixture of citronellal and citronellol poses no problem, since these materials have boiling points differing by some 25° C, so that their separation is quite simple. Under the conditions of the process, there is an almost total absence of the usual impurities, such as tetrahydrocitronellal or isopulegol, so that the formation of mixtures of citronellal and citronellol before dimethyl octanol formation is quite advantageous.

The first step of the hydrogenation of citral to citronellal is quite exothermic. A reaction started at room temperature may quickly reach from 40° to 70° C, depending on the heat losses in the system, if the reaction temperature is left unchecked.

If desired, heat can be supplied to bring the reaction temperature to as high as 200° C and more. Surprisingly, however, the reaction temperature is not critical, since it has not been found to change the yield of the desired products over the range from 5° to 200° C.

Consequently, it is convenient simply to accept the exothermic nature of the reaction, and neither cool the reaction mixture nor supply heat, but instead permit the reaction to proceed at the temperature it wishes to assume, under the reaction conditions. The temperature can be left unchecked until the reaction has been concluded, at which point it may be advisable to cool the reaction mixture, before removing it from the reaction vessel, as a matter of convenience of handling.

The reaction time required to reach any particular combination of reaction products depends on a number of factors, including for example the amount and reactivity of the catalyst, the pressure, the temperature, and the composition of the final product. Consequently, the reaction conditions best adapted for a particular objective are normally determined by trial and error, but will be found to lie within the above parameters.

When one makes citronellol starting from citronellal, natural or synthetic, the hydrogenation is very fast.

Accordingly, it is normally preferred to operate the process in a manner so as to halt the hydrogenation before dimethyl octanol begins to be formed. However, the time selected for halting the hydrogenation will of course depend upon whether citronellal is the only desired product, or whether citronellol is the desired product, or both. One can select any reaction time that gives the desired proportion of citronellal and/or citronellol in the reaction mixture, and then halt the reaction at that stage.

It is possible to carry out the hydrogenation reaction at atmospheric pressure. However, the hydrogenation reaction then proceeds rather slowly. A suitable reaction rate is obtained at from 2 to 5 psi hydrogen pressure. The higher the hydrogen pressure, the more rapid the hydrogenation. Consequently, hydrogenation pressures during the reaction of 10 psi and higher are preferred. Preferably, the hydrogen pressure in the reaction vessel is within the range from about 40 to about 100 psi, but higher pressures can be used, if desired. There is in fact no upper limit except as may be imposed by practicality, and the pressure vessels available. A suggested upper limit is 500 psi.

The following Examples in the opinion of the inventor represent preferred embodiments of the invention.

In most of the Examples, the hydrogenation was carried out in a reactor capable of withstanding elevated temperatures and pressures, equipped with a cooling jacket for temperature control, and sampling ports. Others were carried out in a simple Parr hydrogenator. The reactants were charged to the vessel, the vessel purged with nitrogen, and the atmosphere then replaced by hydrogen, and the desired pressure of hydrogen maintained throughout the reaction. The course of the hydrogenation was followed by analysis of samples removed through the sampling ports.

EXAMPLE 1

In this Example, the reaction materials charged to the pressure vessel were citral 152 g., methanol (0.5% $H_2O$) 30 g., and 12 g. wet chromium-promoted Raney nickel catalyst (available commercially from Davison Division of Grace Chemical Company, Raney nickel catalyst No. 24, composed of a tertiary alloy system of nickel, aluminum and chromium, the nickel and aluminum being in an approximately 1:1 ratio, and containing approximately 1% chromium). After purging with nitrogen and pressurizing with hydrogen, the temperature was allowed to rise to 75° C, and the hydrogen pressure was set at 45 psi, and maintained at this pressure for several hours, while stirring the reaction mixture.

Samples were taken at regular intervals, and analyzed by gas-liquid chromatographic analysis, with the results shown in Table I:

TABLE I

| Time (hrs): | 0.40 | 1 | 2 | 3 | 4 | 5 | 6 | 7 | 8 | 9 | 10 | 11 | 12 |
|---|---|---|---|---|---|---|---|---|---|---|---|---|---|
| Sample No. | 1 | 2 | 3 | 4 | 5 | 6 | 7 | 8 | 9 | 10 | 11 | 12 | 13 |
| Components % | | | | | | | | | | | | | |
| Citral | 57.3 | 3.1 | — | — | — | | | | | | | | |
| Citronellal | 40.5 | 69.2 | 65.5 | 53.8 | 43.9 | 35.1 | 23.8 | 17.6 | 12.1 | 8.1 | 4.6 | 2.6 | 1.3 |
| Citronellol | — | 22.8 | 29.6 | 40.3 | 50.7 | 59.7 | 69.9 | 77.0 | 82.5 | 86.2 | 90.0 | 91.0 | 93.8 |
| Nerol-Geraniol | 1.3 | 4.3 | 4.0 | 4.0 | 4.0 | 4.1 | 4.1 | 4.1 | 4.1 | 4.2 | 4.2 | 4.2 | 4.2 |
| Dimethyl Octanol | — | — | — | 0.1 | 0.1 | 0.2 | 0.3 | 0.4 | 0.5 | 0.5 | 0.5 | 0.5 | 0.5 |

At the end of 12½ hours reaction time, the reaction mixture was cooled, filtered to remove catalyst, and a total of 200 g charged to the bottom of a fractionating column, for fractional distillation.

The distillation yielded a main cut at 86° C and 1 mm vacuum that amounted to 130.5 g, with 2.0 g of residue. The main cut contained 94% citronellol, 4% geraniol/nerol, 1.2% dimethyl octanol, 0.2% citronellal, and 0.4% low boiling components.

It is apparent from the data that if the reaction mixture had been subjected to distillation at the end of two hours of reaction, the mixture would have contained predominantly citronellal, in admixture with citronellol, without dimethyl octanol. The citronellal and citronellol could readily have been separated, and this cut would thereafter have constituted a desirable reaction product.

EXAMPLES 2 TO 5

Example 1 was repeated, varying the amounts of chromium-promoted Raney nickel catalyst, as well as the amount of solvent.

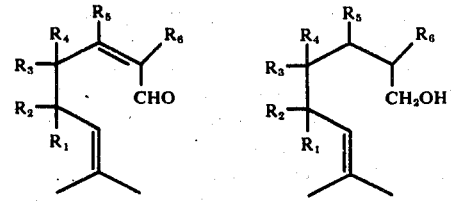

TABLE II

| Example No. | Catalyst g | Solvent ml/mol | Temp C° | Time hrs. | PRODUCT BY GLC ANALYSIS | | | |
|---|---|---|---|---|---|---|---|---|
| | | | | | Citronellal | Citronellol | Nerol Geraniol | DMO* |
| 2 | 8 | 36 | 100 | 5½ | 2.0 | 92.3 | 4 | 0.4 |
| 3 | 5 | 0 | 115 | 4½ | 1.4 | 88.5 | 1.2 | 8.6 |
| 4 | 5 | 5 | 148 | 5½ | 62.3 | 25.6 | 3.9 | 0.2 |
| 5 | 8 | 50 | 40 | 3 | 68.3 | 22 | 2.6 | 0.16 |

*Dimethyl Octanol

It is apparent from these results that a better yield is obtainable in the presence of methanol than in its absence (compare Examples 2, 4 and 5 with 3). Even though the reaction seems to proceed more rapidly, it is less selective, and results in a considerably higher proportion of dimethyl octanol, at an earlier stage of the reaction.

Even the addition of only a very small amount of solvent (Example 4 compared to Example 3) is sufficient to suppress dimethyl octanol formation, at the same time consderably slowing the reaction, even though the reaction temperature is higher.

For comparison purposes, a control run was made substituting 7.5 g conventional Raney nickel catalyst for the chromium-promoted Raney nickel catalyst, and using 36 ml/mol of solvent at 75° C. The following results were obtained: after 20.6 hours there was obtained 33.4% of citronellal and 56% citronellol.

EXAMPLES 6 TO 8

Experiments were run in a Parr apparatus substituting different inert solvents for the methanol and using 4 g chromium-promoted Raney nickel catalyst per mole of citral, with the following results:

TABLE III

| Ex. No. | Solvent[3] | Temp. °C | Pressure PSI | | | Total Reaction Time hrs. | % by Weight GLC Analysis[2] | | | | Direct Yield % | True Yield % |
|---|---|---|---|---|---|---|---|---|---|---|---|---|
| | | | PI[1] | PF[1] | ΔP | | Citronellal | DMO[4] | Citronellol | Nerol/ Geraniol | | |
| 6 | Isopropanol | 25 | 45 | 23.9 | 21.1 | 2.0 | 46.9 | 0.3 | 45.5 | 1.0 | 49.5 | 98.4 |
| 7 | Tetrahydrofuran | 25 | 45 | 26 | 19.0 | 1.3 | 43.1 | 0.4 | 49.5 | 0.9 | 53.7 | 98.5 |
| 8 | Hexane | 25 | 44 | 20.5 | 23.5 | 3.0 | 21.6 | 1.0 | 70.4 | 1.5 | 76.6 | 99.1 |

[1]PI = initial pressure
PF = final pressure
[2]No citral or isopulegol found.
Total time for citral comsumption is 1 hour.
[3]36 ml/mole citral.
[4]Dimethyl octanol It is apparent from the above results that these solvents are equally effective in suppressing dimethyl octanol formation, and result in good yields of citronellol and citronellal.

Having regard to the following disclosure, the following is claimed as the inventive and patentable embodiments thereof:

1. In the process for the hydogenation of unsaturated aldehydes having the formulae:
to form an aldehyde and/or alcohol having the formulae:
wherein $R_1$, $R_2$, $R_3$, $R_4$, and $R_6$ are selected from the group consisting of hydrogen and lower alkyl groups having from one to about five carbon atoms and $R_5$ is a lower alkyl group having from one to about five carbon atoms, which comprises hydrogenating the aldehyde in the presence of catalyst and hydrogen gas, the improvement which comprises carrying out the hydrogenation in the presence of a chromium-promoted Raney nickel catalyst at a temperature within the range from about 5° C to about 200° C, and at a hydrogen pressure within the range from atmospheric pressure to about 500 psi.

2. The process according to claim 1, which comprises carrying out the hydrogenation in the presence of an inert organic solvent.

3. The process according to claim 2 in which the solvent is a lower aliphatic alcohol having from one to about five carbon atoms.

4. The process of claim 1 in which the amount of solvent is at least about 10% up to about 100% by weight of the aldehyde.

5. The process of claim 1, in which the starting aldehyde is citronellal, which is converted to citronellol.

6. The process of claim 1 in which the starting aldehyde is citral, 3,7-dimethyl-2,6-octadiene-al, which is converted to citronellol.

7. The process of claim 1, in which the starting aldehyde is citral, which is converted to a mixture of citronellal and citronellol.

8. The process of claim 1 in which the starting aldehyde is selected from the group consisting of:
3-ethyl-7-methyl-2,6-octadiene-al
3-isobutyl-7-methyl-2,6-octadiene-al
3-amyl-7-methyl-2,6-octadiene-al
2,3,4,5,7-pentamethyl-2,6-octadiene-al
3,5,7-trimethyl-2,6-octadiene-al 3,4,4,5,5,7-hexamethyl-2,6-octadiene-al
2,4,7-trimethyl-3-isopropyl-2,6-octadiene-al
2,3,7 trimethyl-2,6-octadiene-al 9. The process of claim 1 in which the starting aldehyde is selected from the group consisting of:
3-ethyl-7-methyl-6-octene-al
3-isobutyl-7-methyl-6-octene-al
3-amyl-7-methyl-6-octene-al
2,3,4,5,7-pentamethyl-6-octene-al
3,5,7-trimethyl-6-octene-al
3,4,4,5,6,7-hexamethyl-6-octene-al
2,4,7-trimethyl-3-isopropyl-6-octene-al
2,3,7-trimethyl-6-octene-21

10. The process of claim 1 in which the amount of Raney nickel catalyst is within the range from about 0.5% to about 25% by weight of aldehyde.

11. The process of claim 1 in which the hydrogen is at a pressure within the range from atmospheric pressure up to about 100 psi.

12. The process of claim 1 in which the reaction mixture is agitated under a hydrogen atmosphere until absorption of hydrogen ceases, the hydrogenation of the olefinic group in a conjugated position to the carbonyl group has been substantially completed, the catalyst is removed, and the hydrogenated reaction product recovered.

13. The process of claim 1 in which the reaction mixture is agitated under a hydrogen atmosphere until absorption of hydrogen ceases, and the hydrogenation of the aldehyde group has been substantially completed, the catalyst is removed, and the hydrogenated reaction product recovered.

14. The process of claim 1 in which the reaction mixture is agitated under a hydrogen atmosphere until absorption of hydrogen ceases, and the hydrogenation of the olefinic group in a conjugated position to the carbonyl group and of the carbonyl group have been substantially completed, the catalyst is removed, and the hydrogenated reaction product removed.

15. The process of claim 1 in which the reaction is carried out at a temperature within the range from about 20° to about 100° C.

* * * * *

UNITED STATES PATENT OFFICE
CERTIFICATE OF CORRECTION

Patent No. 4,029,709　　　　　　　Dated June 14, 1977

Inventor(s) Robert S. De Simone et al

It is certified that error appears in the above-identified patent and that said Letters Patent are hereby corrected as shown below:

Column 1, line 34　：　"Burgarian" should be --Bulgarian--

Column 1, line 52　：　"ocadiene" should be --octadiene--

Column 2, line 5　：　Name below third formula in line 18 is incorrect

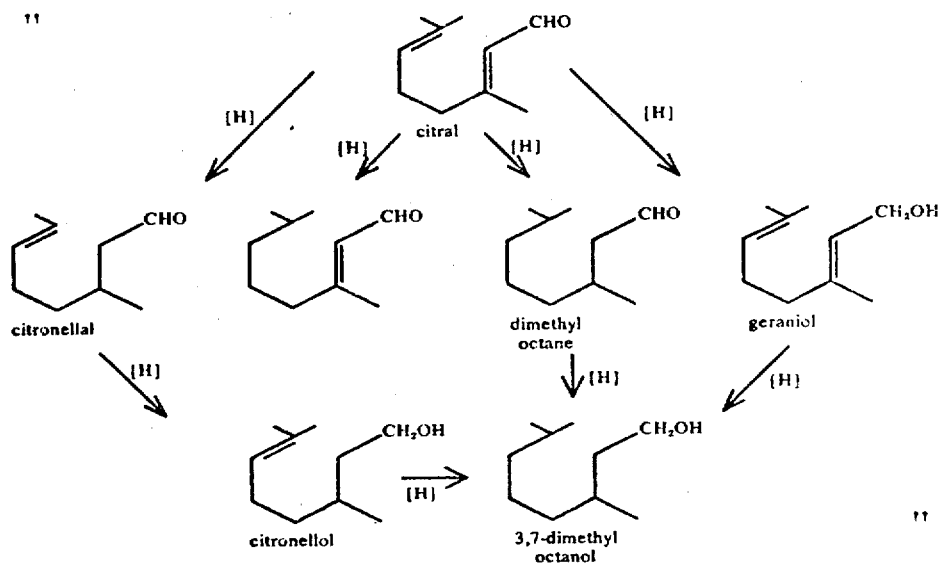

This name should be corrected as follows:

UNITED STATES PATENT OFFICE
CERTIFICATE OF CORRECTION

Patent No. 4,029,709      Dated June 14, 1977

Inventor(s) Robert S. De Simone et al

It is certified that error appears in the above-identified patent and that said Letters Patent are hereby corrected as shown below:

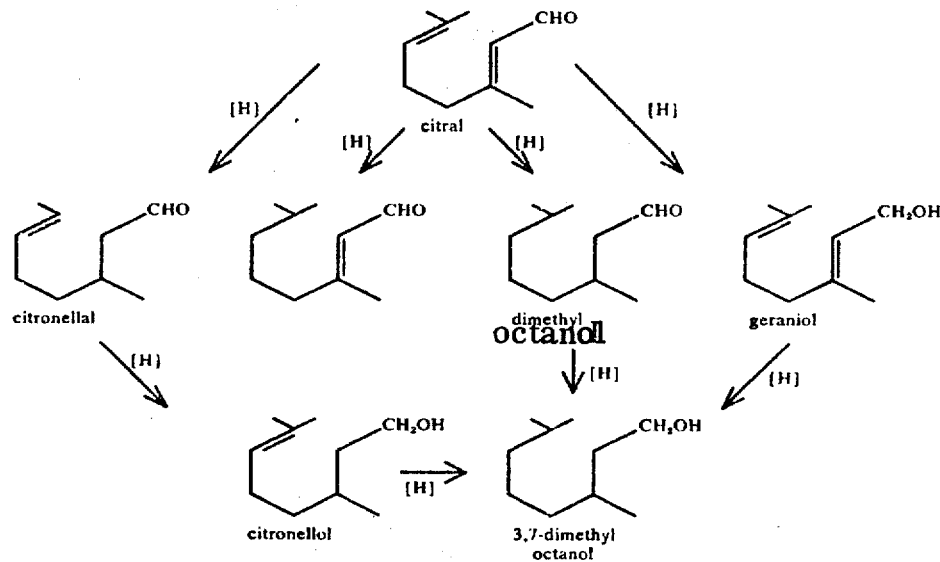

| | |
|---|---|
| Column 2, line 43 : | "retrol" should be -- retro -- |
| line 60 : | "citronella" should be -- citronellal-- |
| Column 4, line 65 : | "citronelal" should be -- citronellal -- |
| Column 6, line 27 : | Please insert -- isopropanol-- after "propanol" |
| Column 7, line 68 : | "hydrogenation", second occurrence, should be -- hydrogen -- |
| Column 8, line 67 : | "thereafter" should be --therefore-- |
| Column 9, line 10 : | Table II under heading Time Hrs: "5 ½", first occurrence, should be -- 8½ -- |

UNITED STATES PATENT OFFICE
CERTIFICATE OF CORRECTION

Patent No. 4,029,709　　　　　　　　Dated June 14, 1977

Inventor(s) Robert S. De Simone et al

It is certified that error appears in the above-identified patent and that said Letters Patent are hereby corrected as shown below:

Column 9, line 66　:　Please insert the following missing formulae:

-- 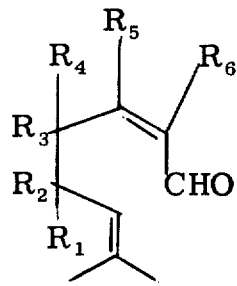　　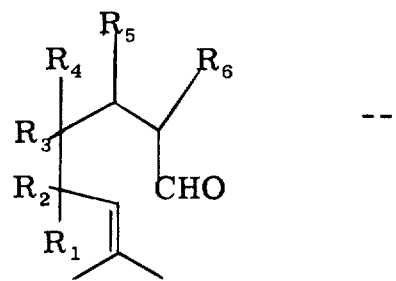 --

Column 12, line 18　:　"removed" should be -- recovered --

Signed and Sealed this

Fourth Day of October 1977

[SEAL]

*Attest:*

RUTH C. MASON
*Attesting Officer*

LUTRELLE F. PARKER
*Acting Commissioner of Patents and Trademarks*